(12) United States Patent
Qiu et al.

(10) Patent No.: US 10,274,479 B2
(45) Date of Patent: Apr. 30, 2019

(54) METHOD FOR SPERM MOTILITY EVALUATION AND SCREENING AND ITS MICROFLUIDIC DEVICE

(75) Inventors: Tian Qiu, Beijing (CN); Rui Ma, Beijing (CN); Chao Han, Beijing (CN); Lan Xie, Beijing (CN); Jing Cheng, Beijing (CN)

(73) Assignee: CapitalBio Corporation, Beijing (CN)

(*) Notice: Subject to any disclaimer, the term of this patent is extended or adjusted under 35 U.S.C. 154(b) by 932 days.

(21) Appl. No.: 14/117,597

(22) PCT Filed: Jun. 1, 2012

(86) PCT No.: PCT/CN2012/000753
§ 371 (c)(1),
(2), (4) Date: Mar. 17, 2014

(87) PCT Pub. No.: WO2012/163087
PCT Pub. Date: Dec. 6, 2012

(65) Prior Publication Data
US 2014/0199720 A1  Jul. 17, 2014

(30) Foreign Application Priority Data
Jun. 3, 2011 (CN) .......................... 2011 1 0148748

(51) Int. Cl.
*B01L 3/00* (2006.01)
*A61B 17/43* (2006.01)
*G01N 33/50* (2006.01)

(52) U.S. Cl.
CPC ......... *G01N 33/5005* (2013.01); *A61B 17/43* (2013.01); *B01L 3/502746* (2013.01); *B01L 3/502761* (2013.01); *B01L 2200/0652* (2013.01); *B01L 2300/0825* (2013.01)

(58) Field of Classification Search
None
See application file for complete search history.

(56) References Cited

U.S. PATENT DOCUMENTS

| | | | |
|---|---|---|---|
| 5,427,946 A | 6/1995 | Kricka et al. | |
| 5,637,469 A * | 6/1997 | Wilding | B01F 15/0264 366/DIG. 3 |
| 6,193,647 B1 | 2/2001 | Beebe et al. | |
| 6,448,069 B1 | 9/2002 | Cecchi et al. | |
| 6,900,021 B1 * | 5/2005 | Harrison | B01J 19/0093 422/504 |
| 8,658,418 B2 * | 2/2014 | Daridon | C12M 1/34 435/288.5 |
| 2003/0017467 A1 | 1/2003 | Hooper et al. | |
| 2004/0142411 A1 | 7/2004 | Kirk et al. | |
| 2006/0270021 A1 * | 11/2006 | Takayama | B01L 3/50273 435/283.1 |
| 2007/0259424 A1 * | 11/2007 | Toner | B01L 3/502746 435/372 |
| 2007/0264705 A1 | 11/2007 | Dodgson | |
| 2010/0111770 A1 | 5/2010 | Hwang et al. | |
| 2010/0291535 A1 * | 11/2010 | Yao | C12N 5/0612 435/2 |
| 2011/0061472 A1 * | 3/2011 | Wo | G01N 35/00 73/863.21 |
| 2011/0183312 A1 | 7/2011 | Huang | |
| 2012/0118740 A1 * | 5/2012 | Garcia | B03C 5/005 204/547 |
| 2014/0248656 A1 * | 9/2014 | Demirci | G01N 33/5029 435/30 |
| 2014/0315281 A1 * | 10/2014 | Pan | C12M 21/06 435/283.1 |

FOREIGN PATENT DOCUMENTS

| | | |
|---|---|---|
| CN | 1909847 | 2/2007 |
| CN | 101597568 | 12/2009 |
| CN | 101827931 | 9/2010 |
| CN | 101914435 | 12/2010 |
| CN | 102242055 | 11/2011 |
| TW | 201040524 | 11/2010 |
| TW | 201109654 | 3/2011 |
| WO | WO-2004/108011 | 12/2004 |
| WO | WO-2009/006933 | 1/2009 |
| WO | WO-2009/062095 | 5/2009 |
| WO | WO-2012/019436 | 2/2012 |

OTHER PUBLICATIONS

Samper, Oviductal Epithelial Cells: Can they select better sperm, Sep. 22, 2008.*
Seo et al., Development of sorting, aligning, and orienting motile sperm using microfluidic device operated by hydrostatic pressure, Microfluid Nanofluid (2007) 3:561-570.*
Bungum et al., "Sperm chromatin structure assay (SCSA): a tool in diagnosis and treatment of infertility," Asian J Androl (2011) 13:69-75.
Fuhr et al., "High-frequency electric field trapping of individual human spermatozoa," Hum Reprod (1998) 13(1):136-141.
International Preliminary Report on Patentability issued for PCT/CN2012/000753, dated Dec. 4, 2013, 8 pages.
International Search Report and Written Opinion issued for PCT/CN2012/000753, dated Sep. 13, 2012, 13 pages.
Kricka et al., "Applications of a microfabricated device for evaluating sperm function," Clin Chem (1993) 39:1944-1947.

(Continued)

*Primary Examiner* — Taeyoon Kim
*Assistant Examiner* — Srikanth Patury
(74) *Attorney, Agent, or Firm* — Rimon, P.C.

(57) ABSTRACT

The present invention provides a microfluidic device and its use for cell motility classification. The microfluidic device comprises a fluid inlet, a sample inlet and a channel connecting the fluid inlet and the sample inlet, wherein the channel comprises at least two sections of different sizes, and the channel allows fluid flow from the fluid inlet to the sample inlet.

30 Claims, 3 Drawing Sheets

(56) References Cited

OTHER PUBLICATIONS

Ohta et al., "Motile and non-motile sperm diagnostic manipulation using optoelectronic tweezers," Lab Chip (2010) 10(23):3213-3217.
Xie et al., "Integration of sperm motility and chemotaxis screening with a microchannel-based device," Clin Chem (2010) 56(8):1270-1278.
Restriction Requirement for U.S. Appl. No. 13/814,426, dated Oct. 28, 2014, 11 pages.
Response to Restriction Requirement for U.S. Appl. No. 13/814,426, dated Dec. 18, 2014, 8 pages.
Non-final Rejection for U.S. Appl. No. 13/814,426, dated Jan. 23, 2015, 8 pages.
Notice of Abandonment for U.S. Appl. No. 13/814,426, dated Aug. 17, 2015, 2 pages.
Restriction Requirement for U.S. Appl. No. 13/991,848, dated Apr. 30, 2014, 11 pages.
Response to Restriction Requirement for U.S. Appl. No. 13/991,848, dated Jun. 18, 2014, 7 pages.
Non-final Rejection for U.S. Appl. No. 13/991,848, dated Sep. 30, 2014, 9 pages.
Response to Non-final Rejection for U.S. Appl. No. 13/991,848, dated Jan. 30, 2015, 14 pages.
Final Rejection for U.S. Appl. No. 13/991,848, dated Apr. 7, 2015, 8 pages.
Response to Final Rejection for U.S. Appl. No. 13/991,848, dated Jun. 5, 2015, 11 pages.
Advisory Action for U.S. Appl. No. 13/991,848, dated Jul. 10, 2015, 3 pages.
Request for Continued Examination for U.S. Appl. No. 13/991,848, dated Oct. 5, 2015, 15 pages.
Non-Final Rejection for U.S. Appl. No. 13/991,848, dated Apr. 7, 2016, 7 pages.
Response to Non-Final Rejection for U.S. Appl. No. 13/991,848, dated Jul. 7, 2016, 9 pages.
Notice of Allowance for U.S. Appl. No. 13/991,848, dated Jul. 26, 2016, 7 pages.
Farooq et al., "A modified procedure for isolation of astrocyte- and neuron-enriched fractions from rat brain," J Neurochem (1978) 31(4):887-894.
International Preliminary Report on Patentability and Written Opinion for PCT/CN2012/000065, dated Jul. 16, 2013, 5 pages.
International Search Report for PCT/CN2012/000065, dated Mar. 29, 2012, 5 pages.
McCarthy et al., "Preparation of separate astroglial and oligodendroglial cell cultures from rat cerebral tissue," J Cell Biol (1980) 85(3):890-902.
Whitesides, "The origins and the future of microfluidics," Nature (2006) 442:368-373.
International Search Report for PCT/CN2011/001329, dated Nov. 17, 2011, 3 pages.
Koyama et al., "Chemotaxis assays of mouse sperm on microfluidic devices," Anal. Chem. (2006) 78:3354-9.
Written Opinion for PCT/CN2011/001329, dated Nov. 17, 2011, 7 pages.
Xie et al., "Integration of sperm motility and chemotaxis screening with a microchannel-based device," Clinical Chemistry (2010) 56(8):1270-1278.

\* cited by examiner

METHOD FOR SPERM MOTILITY EVALUATION AND SCREENING AND ITS MICROFLUIDIC DEVICE

CROSS-REFERENCE TO RELATED APPLICATIONS

This application is the national phase of PCT application PCT/CN2012/000753 having an international filing date of Jun. 1, 2012, which claims priority to Chinese Patent Application No. 201110148748.2, filed on Jun. 3, 2011. The entire contents of the above-listed applications are incorporated herein by this reference in their entireties.

TECHNICAL FIELD

The present invention relates to a microfluidic device, e.g., an integrated microfluidic device, and uses thereof, particularly a micro fluidic device for evaluation and screening of sperm motility, using fluid of different flow rates.

BACKGROUND ART

The assessment of sperm motility is an indispensable means in the clinical diagnosis of male infertility. "Laboratory Manual For The Examination Of Human Semen And Sperm-Cervical Mucus Interaction" published by the World Health Organization (WHO) indicates several commonly used indicators of the clinical testing of sperm, including density test, morphological test and motility test. The criteria of sperm motility are as follows: Class a, progressive motility (≥25 μm/s straight line velocity at 37° C.); Class b, non-linear motility (5-25 μm/s straight line velocity at 37° C.); Class c, non-progressive (0-5 μm/s straight line velocity at 37° C.); Class d, immotile. The existing method of detection utilizes video recording by a microscope combined with Computer-aided Sperm Analysis (CASA) software to evaluate sperm motility. However, the existing microscopic observation method can only be used in the evaluation of sperm, but cannot screen and separate sperm in specific velocity range for subsequent in vitro fertilization (IVF) or research purposes.

The microfluidic chips have great potentials in the evaluation and screening of sperm. The flexible design of various micro-channel and micro-structure on a microfluidic chip makes it easy to mimic the physiological condition, manipulate or position the sperm, and control the fertilization process; in addition, because of the advantages of integration on a microfluidic chip, multi-parameter detection of sperm can be integrated on a single chip.

In 1993, Kricka el al. from University of Pennsylvania used a microfluidic chip to evaluate the motility of sperm for the first time (Kricka et al., *Clin. Chem.* (1993) 39: 1944-7). In 2004, researchers from University of Michigan filed a patent application (PCT Patent Publication No. WO 2004/108011 A1) to screen sperm with higher motility in a microfluidic chip, in which interfaces of fluid was achieved because of laminar flow in micro fluidics, so that sperm with higher motility can swim through the interface and reach the target region to be transported to the outlet pool. However, the methods disclosed in this patent application cannot screen sperm within a specific velocity range; besides, the chip has two inlets and two outlets and the fluid interface needs to be stable, thus the structure and the operation of the chip are both complicated. In 2004, researchers at National Taiwan University filed a patent application (U.S. Patent Publication No. 2011/0061472 A1) for the evaluation and screening of motile sperms, in which fluid flow was used against sperm swimming. Only sperms with high motility could reach the contracted region of the channel and be transported to the outlet. However, the fluid direction in the contracted region was the same as sperm swimming direction. The chip did not implement the capabilities of evaluating, screening and capturing sperm in different motility ranges. In addition, the contracted region was too narrow and only allowed one sperm to pass at a time, greatly reducing the throughput of sperm evaluation and screening.

In 1998, G. Fuhr el al. from Humboldt University, Germany reported a micro-electrode chip in *Human Reproduction*. (Fuhr et al., *Hum. Reprod.* (1998) 13: 136 41) They utilized negative dielectrophoresis to capture single sperm and they could capture sperm of different motility by applying different electrical field force. In 2010, A. Ohta et al. from University of Hawaii reported a micro-electrode chip with an integrated optical system in Lab on a Chip. (Ohta et al., *Lab Chip.* (2010) 10: 3213-7) The chip exerted force on sperm by optical tweezers in order to distinguish live and dead sperms. However, such methods using electric field force or light field force to screen and manipulate sperm may harm the sperm and make an impact of the health of the sperm during screening, which may result in the failure of subsequent in vitro fertilization or research work.

In recent years, a growing number of researchers found that clinical routine tests of sperm density, morphology and motility are not competent enough to reveal male reproductive capacity (e.g., Mona Bungum et al., *Asian Journal of Andrology* (2011) 13: 69 75). The latest research showed that parameters such as DNA integrity, acrosome ability, chemotaxis, etc. seriously affect the fertilizing capacity of sperm (Xie et al., *Clin. Chem.* (2010) 56: 1270-8). In other words, the fastest sperms may not be the sperm with the strongest fertilizing capacity. Hence the motility classification of sperm and the capture and screening of sperm in different velocity range are of great significance.

SUMMARY OF THE INVENTION

The present invention relates to a microfluidic device, e.g., an integrated microfluidic device, and its use for cell motility classification. Therefore, in one aspect, provided herein is a microfluidic device for classification of the motility of a cell, which microfluidic device comprises a fluid inlet, a sample inlet and a channel connecting said fluid inlet and said sample inlet, wherein said channel comprises at least two sections of different sizes, and said channel allows fluid flow from said fluid inlet to said sample inlet.

In some embodiments, the channel sections with different sizes may have different cross-sectional areas. In some embodiments, the channel sections with different sizes may comprise barriers of different sizes, numbers and/or arrangements. In some embodiments, the size of the sections may increase successively from the fluid inlet to the sample inlet, and the largest section may be connected to the sample inlet. In some embodiments, the smallest section of the channel may be connected to the fluid inlet. In some embodiments, the smallest section of the channel may be connected to the fluid inlet through a first fluid stabilizing channel. In some embodiments, the size of the first fluid stabilizing channel may be larger than the smallest section of the channel. In some embodiments, the adjacent sections of different sizes may be connected directly to each other. In some embodiments, the adjacent sections of different sizes may be connected through a second fluid stabilizing channel. In some embodiments, the size of the second fluid stabilizing channel may be constant or variant. In some embodiments, the size of the second fluid stabilizing channel may be larger than the smaller section of the two adjacent sections of the channel. In some embodiments, the channel may comprise three sections of different sizes. In some embodiments, the ratio of the sizes of the three different channel sections may be about 0.24:1:1.74. In some embodiments, the barriers may comprise epithelial cells, preferably oviduct epithelial cells. In some embodiments, the channel may be covered by epithelial cells, preferably oviduct epithelial cells. In some embodiments, the cross section of the channel may be rectangular, circular, or another shape.

In some embodiments, the microfluidic device may further comprise a cell culture medium. In some embodiments, the cell culture medium may flow in the channel, preferably from the fluid inlet to the sample inlet. In some embodiments, the flow rate of the cell culture medium may vary in different sections of the channel. In some embodiments, the maximum flow rate of the cell culture medium may be about 20-220 µm/s. In some embodiments, the maximum flow rate of the cell culture medium may be about 20 µm/s. In some embodiments, the microfluidic device may further comprise a cell in the cell culture medium. In some embodiments, the cell may be a sperm. In some embodiments, a chemo-attractant may be applied in the fluid inlet. In some embodiments, the chemo-attractant may be progesterone or glucose. In some embodiments, the channel may comprise at least two electrodes. In some embodiments, the micro fluidic device may comprise two or more channels. In some embodiments, the channels may be radially arranged and/or connect to the fluid inlet.

Further provided herein is a microfluidic system for classifying cell motility, which comprises the microfluidic device disclosed herein and an apparatus to apply force to the cell culture medium. In some embodiments, the microfluidic system may further comprise a device to measure the motility of the cells. In some embodiments, the device may be a camera or video recorder.

In another aspect, the present invention provides a method of classifying the motility of a cell using a microfluidic device disclosed herein, comprising: a) adding a cell culture medium in the fluid inlet; b) adding cells in the sample inlet; c) applying an external force to the cell culture medium to achieve a flow rate; and d) measuring the motility of the cells moving against the flow of the culture medium in the channel.

In some embodiments, the cells with different motilities may locate in different sections of the channel. In some embodiments, a chemo-attractant may be applied in the fluid inlet, wherein the chemo-attractant may be progesterone or glucose. In some embodiments, the channel may comprise at least two electrodes. In some embodiments, the motility of the cells may be measured by taking pictures or videos of the cells in the channel. In some embodiments, the motility of the cells may be measured by the location of the cells in different sections of the channel. In some embodiments, the flow of the cell culture medium may be stopped to let the cells move to the fluid inlet.

In some embodiments, an external force may be applied to the cells, wherein the external force may be an electrical force, an optical force or a fluidic force. In some embodiments, the cells with a specific motility may be retrieved. In some embodiments, the cells may be sperms. In some embodiments, the sperm may be used for in vitro fertilization.

DETAILED DESCRIPTION OF THE INVENTION

This invention provides a microfluidic device and its uses for cell motility classification and screening.

In some embodiments, the microfluidic device disclosed herein can be used as the following steps:

1) Form a stable flow field of different velocities in the micro-channel. Add medium in the inlet and form different flow field because of the difference in the channel's cross-sectional areas.

2) Sperm screening process. Add sperms in the sperm inlet. Sperms swim towards the inverse direction of the fluid flow. When the straight-line velocity (VSL) of a sperm is the same as the flow velocity, the sperm will be captured. Over a period of time, sperms of different velocities will be captured in different sections of the channel.

3) Recording process of the result. Take pictures or videos of the sperm by bright field microscopy or fluorescence staining. Then count the sperm number, e.g., by human eye or computer. Sperm motion parameters can also be analyzed, e.g., by taking pictures or videos, when the fluid influx is stopped and sperm swim in static fluid field.

4) Sperm retrieval or transportation process. For sperm capture in accordance with the motility classification, sperms can be retrieved in the outlet pool after transporting them there by sperm's own swimming or applying electric field force, light field force, fluid force for consequent in vitro fertilization or research. Another method is to transport the sperm to a specific zone on the chip by the above mentioned methods and complete the in vitro fertilization or other research on the chip.

In the above step 4), after sperm motility classification, sperm can be transported to the outlet pool by sperm's own swimming or applying electric field force, light field force, fluid force and exits the chip from the outlet for consequent in vitro fertilization or research.

In the above step 4), after sperm motility classification, sperm can be transported to a specific zone on the chip by sperm's own swimming or applying electric field force, light field force, fluid force and implement the consequent in vitro fertilization or research.

In the above step 1) or 4), sperm can be attracted to swim towards the outlet pool by adding chemo-attractant in the outlet pool.

In some embodiments, various sections with different cross sections are achieved in one microfluidic channel to generate fluid flow field of different velocities. Sperms swim towards the inverse direction of the fluid flow, and when a sperm's straight-line velocity (VSL) equals the local flow velocity, the combined velocity will be zero, so that the sperm may be then captured in the corresponding region.

The microfluidic device has a wide arrange of applications, including but not limited to: detection of human sperm for male infertility diagnosis; screening of the human sperm for the field of assisted reproduction; the detection and screening of animal sperm for breeding; detection and screening of human or animal sperm for scientific research on biological mechanism; motility screening and mechanism research of other cells or organisms that swim spontaneously.

Because of the technologies mentioned above, the present invention has numerous advantages: 1. The microfluidic device in some embodiments forms the fluid field with different flow velocities by changing the cross section of the channel, which is a simple structure, easy to fabricate and easy to operate. 2. The microfluidic device with different flow velocities by changing the cross section of the channel mimics a physiological environment. It is less harmful to sperms comparing with other methods, e.g., optical or electrical force etc., which is crucial for the success of subsequent in vitro fertilization and the revealing of the real status of sperm during scientific research. 3. The motility classification of sperms in the present microfluidic device is more quantitative. The statistical analysis of sperm percentage in each section facilitates male infertility diagnostics; while the retrieval of sperm in a specific velocity range meets the demand of assisted reproductive medicine and reproductive biology research. 4. The present microfluidic device achieves sperm motility screening, which can be integrated with other parameters on a single chip, in order to achieve multi-parameter sperm evaluation and screening.

In conclusion, the micro fluidic chip in the present invention has advantages including low cost, multi-parameter integration and easy to manipulation. Thus, it has wide applications in human or animal sperm evaluation and screening, motility screening of other cells or organisms that swim spontaneously, and also in the field of assisted reproductive medicine and fertilization mechanism research. Other exemplary cells and organisms include human, animal, plant or microbial cells and organisms.

A. DEFINITIONS

Unless defined otherwise, all technical and scientific terms used herein have the same meaning as is commonly understood by one of ordinary skill in the art to which this invention belongs. All patents, applications, published applications and other publications referred to herein are incorporated by reference in their entireties. If a definition set forth in this section is contrary to or otherwise inconsistent with a definition set forth in the patents, applications, published applications and other publications that are herein incorporated by reference, the definition set forth in this section prevails over the definition that is incorporated herein by reference.

As used herein, the singular forms "a", "an", and "the" include plural references unless indicated otherwise. For example, "a" dimer includes one or more dimers.

As used herein, the term "microfluidic device" generally refers to a device through which materials, particularly fluid borne materials, such as liquids, can be transported, in some embodiments on a micro-scale, and in some embodiments on a nanoscale. Thus, the microfluidic devices described by the presently disclosed subject matter can comprise microscale features, nanoscale features, and combinations thereof.

Accordingly, an exemplary micro fluidic device typically comprises structural or functional features dimensioned on the order of a millimeter-scale or less, which are capable of manipulating a fluid at a flow rate on the order of a μL/min or less. Typically, such features include, but are not limited to channels, fluid reservoirs, reaction chambers, mixing chambers, and separation regions. In some examples, the channels include at least one cross-sectional dimension that is in a range of from about 0.1 μm to about 500 μm. The use of dimensions on this order allows the incorporation of a greater number of channels in a smaller area, and utilizes smaller volumes of fluids.

A microfluidic device can exist alone or can be a part of a microfluidic system which, for example and without limitation, can include: pumps for introducing fluids, e.g., samples, reagents, buffers and the like, into the system and/or through the system; detection equipment or systems; data storage systems; and control systems for controlling fluid transport and/or direction within the device, monitoring and controlling environmental conditions to which fluids in the device are subjected, e.g., temperature, current, and the like.

As used herein, the terms "channel," "micro-channel," "fluidic channel," and "microfluidic channel" are used interchangeably and can mean a recess or cavity formed in a material by imparting a pattern from a patterned substrate into a material or by any suitable material removing technique, or can mean a recess or cavity in combination with any suitable fluid-conducting structure mounted in the recess or cavity, such as a tube, capillary, or the like. In the present invention, channel size means the cross-sectional area of the microfluidic channel.

As used herein, the terms "flow channel" and "control channel" are used interchangeably and can mean a channel in a microfluidic device in which a material, such as a fluid, e.g., a gas or a liquid, can flow through. More particularly, the term "flow channel" refers to a channel in which a material of interest, e.g., a solvent or a chemical reagent, can flow through. Further, the term "control channel" refers to a flow channel in which a material, such as a fluid, e.g., a gas or a liquid, can flow through in such a way to actuate a valve or pump.

As used herein, "chip" refers to a solid substrate with a plurality of one-, two- or three-dimensional micro structures or micro-scale structures on which certain processes, such as physical, chemical, biological, biophysical or biochemical processes, etc., can be carried out. The micro structures or micro-scale structures such as, channels and wells, electrode elements, electromagnetic elements, are incorporated into, fabricated on or otherwise attached to the substrate for facilitating physical, biophysical, biological, biochemical, chemical reactions or processes on the chip. The chip may be thin in one dimension and may have various shapes in other dimensions, for example, a rectangle, a circle, an ellipse, or other irregular shapes. The size of the major surface of chips of the present invention can vary considerably, e.g., from about 1 mm$^2$ to about 0.25 m$^2$. Preferably, the size of the chips is from about 4 mm$^2$ to about 25 cm$^2$ with a characteristic dimension from about 1 mm to about 5 cm. The chip surfaces may be flat, or not flat. The chips with non-flat surfaces may include channels or wells fabricated on the surfaces.

The terms "chemoattractants" and "chemorepellents" refer to inorganic or organic substances possessing chemotaxis-inducer effect in motile cells. Effects of chemoattractants are elicited via chemotaxis receptors, and the chemoattractant moiety of a ligand is target cell specific and concentration dependent. Most frequently investigated chemoattractants are formyl peptides and chemokines. Responses to chemorepellents result in axial swimming and they are considered a basic motile phenomenon in bacteria. The most frequently investigated chemorepellents are inorganic salts, amino acids and some chemokines.

It is understood that aspects and embodiments of the invention described herein include "consisting" and/or "consisting essentially of" aspects and embodiments.

Other objects, advantages and features of the present invention will become apparent from the following specification taken in conjunction with the accompanying drawings.

B. MICROFLUIDIC DEVICE AND MICROFLUIDIC SYSTEM

One objective of the present invention is to provide a microfluidic device, to solve the above mentioned problem of existing technology in evaluating and screening sperms in specific velocity ranges.

To achieve the above mentioned objective, the present invention provides a microfluidic device for classification of the motility of a cell, which microfluidic device comprises a fluid inlet, a sample inlet and a channel connecting said fluid inlet and said sample inlet, wherein said channel comprises at least two sections of different sizes, and said channel allows fluid flow from said fluid inlet to said sample inlet. In some embodiments, the micro fluidic device may further comprise an outlet for the collection and/or retrieval of the cells, which may be the fluid inlet. In some embodiments, the microfluidic device may further comprise a target zone where the cells may be used for further study or operation, e.g., in vitro fertilization.

The channel may have any number of sections of different sizes in any suitable arrangement. The number of channel sections with different sizes may be 2, 3, 4, 5 or more, preferably 3. The ratio of the sizes of 3 different channel sections may be according to the sperm motility classification criteria in "Laboratory Manual For The Examination Of Human Semen And Sperm-Cervical Mucus Interaction" published by the WHO. The cross-sectional area of the 3 sections may have a preferred ratio of about 0.24:1:1.74.

In some embodiments, the size of the sections may increase successively from the fluid inlet to the sample inlet, and the largest section may be directly connected to the sample inlet. In some embodiments, there may be 2 or more than 2 radially arranged microfluidic channels with a common fluid inlet in the microfluidic chip. In some embodiments, the smallest section of the microfluidic channel may be connected directly with the fluid inlet. In some embodiments, the smallest section of the microfluidic channel may be connected to the fluid inlet through a first fluid stabilizing channel and the preferred size of the first fluid stabilizing channel is larger than the smallest section of the channel.

In the above mentioned at least 2 sections of different sizes, the adjacent sections may be connected directly or connected through a second fluid stabilizing channel; the size of the second fluid stabilizing channel may be constant or change gradually. In some embodiments, the size of the second fluid stabilizing channel may be larger than the smaller section of the two adjacent sections.

Normally, the channel sections with different sizes have different cross-sectional areas. The different cross-sectional areas result in a fluid field with different fluid velocities in different sections. The cross section of the said channel may be rectangular or circular. When the cross section is rectangular, the area may be changed by the channel width, depth or both; when the cross section is circle, the area may be changed by the channel diameter; when the cross section is in another shape, the area may be changed by the corresponding size of the cross section.

Alternatively, different cross-sectional areas may be realized by adding barriers of different sizes, numbers and/or arrangements in different sections. The barriers may be epithelial cells, which are preferred as oviduct epithelial cells from human or another animal. In order to mimic the physiological condition in vivo, the microfluidic channel wall may be covered by epithelial cells, which are preferred as oviduct epithelial cells from human or another animal.

Any suitable chemoattractants and/or chemorepellents may be used for the cell motility testing. In some embodiments, both a chemoattractant and a chemorepellent may be added to an outlet pool, or separate outlet pools. A chemoattractant and a chemorepellent may be added to one of the outlet pools simultaneously, or consecutively. The chemoattractant or chemorepellent may be added in the outlet pool or the inlet pool, and both may be added in a single outlet pool or inlet pool. More than one chemoattractants and/or chemorepellent may be added to an exemplary microfluidic system, and each chemoattractant and/or chemorepellent may form a gradient along the length of one of the channels. The chemo-attractant may be progesterone, growth factor or glucose. The most explicit material to attract sperm is progesterone, and growth factor or glucose may be used to attract other cells or bacteria.

In some embodiments, at least 2 electrodes can be constructed in order to transport sperm to the fluid inlet by electrical force.

Exemplary microfluidic devices may comprise a central body structure in which various microfluidic elements are disposed. The body structure includes an exterior portion or surface, as well as an interior portion which defines the various microscale channels and/or chambers of the overall microfluidic device. For example, the body structure of an exemplary microfluidic devices typically employs a solid or semi-solid substrate that may be planar in structure, i.e., substantially flat or having at least one flat surface. Suitable substrates may be fabricated from any one of a variety of materials, or combinations of materials. Often, the planar substrates are manufactured using solid substrates common in the fields of microfabrication, e.g., silica-based substrates, such as glass, quartz, silicon or polysilicon, as well as other known substrates, i.e., gallium arsenide. In the case of these substrates, common microfabrication techniques, such as photolithographic techniques, wet chemical etching, micromachining, i.e., drilling, milling and the like, may be readily applied in the fabrication of microfluidic devices and substrates. Alternatively, polymeric substrate materials may be used to fabricate the devices of the present invention, including, e.g., polydimethylsiloxanes (PDMS), polymethylmethacrylate (PMMA), polyurethane, polyvinylchloride (PVC), polystyrene, polysulfone, polycarbonate and the like. In the case of such polymeric materials, injection molding or embossing methods may be used to form the substrates having the channel and reservoir geometries as described herein. In such cases, original molds may be fabricated using any of the above described materials and methods.

The channels and chambers of an exemplary device are typically fabricated into one surface of a planar substrate, as grooves, wells or depressions in that surface. A second planar substrate, typically prepared from the same or similar material, is overlaid and hound to the first, thereby defining and sealing the channels and/or chambers of the device. Together, the upper surface of the first substrate, and the lower mated surface of the upper substrate, define the interior portion of the device, i.e., defining the channels and chambers of the device. In some embodiments, the upper layer may be reversibly bound to the lower layer.

Further provide herein is a microfluidic system for classifying cell motility, which comprises the microfluidic device disclosed herein and an apparatus to apply force to the cell culture medium.

Exemplary systems may also include sample sources that are external to the body of the device per se, but still in fluid communication with the sample loading channel. In some embodiments, the system may further comprise an inlet and/or an outlet to the micro-channel. In some embodiments, the system may further comprise a delivering means to introduce a sample to the micro-channel. In some embodiments, the system may further comprise an injecting means to introduce a liquid into the micro-channel. Any liquid manipulating equipments, such as pipettes, pumps, etc., may be used as an injecting means to introduce a liquid to the micro-channel.

C. METHODS FOR CELL MOTILITY CLASSIFICATION AND/OR SCREENING

In another aspect, the present invention provides a method of classifying the motility of a cell using a microfluidic device disclosed herein, comprising: a) adding a cell culture medium in the fluid inlet; b) adding cells in the sample inlet; c) applying an external force to the cell culture medium to achieve a flow rate; and d) measuring the motility of the cells moving against the flow of the culture medium in the channel. In some embodiments, at least 10, 100, 1000, 10,000 or more cells subject to the cell motility classification are added to the sample inlet.

Further provided herein is a method to transport sperms with a specific velocity to the target zone of the microfluidic device. The method that transports sperms may comprise: after the disclosed method of motility classification, the sperms with different motility arrive at the target zone of the microfluidic chip at different points. In some embodiments, sperms with different motilities arriving at the target zone of the integrated microfluidic chip at different points may be realized by stopping the injected flow of cell culture medium from the fluid inlet, and letting the sperms swim to the target zone spontaneously. Alternatively, cells with different motility arriving at the target zone of the integrated microfluidic chip at different points may be realized by transporting them by external force; wherein the preferred external force may be electrical force, optical force or fluidic force. When applying external force, it may not be necessary to stop the influx of cell culture medium from the fluid inlet.

Methods for retrieval of spontaneously swimming cells in a specific velocity range also belong to the scope of protection of the present invention, wherein the fluid inlet may be used as the target zone. The microfluidic device and methods disclosed herein for the retrieval of sperm of a specific velocity for in vitro fertilization also belong to the scope of protection of the present invention, wherein the target zone may be the zone for in vitro fertilization in the integrated microfluidic device.

D. EXAMPLES

The following examples are offered to illustrate but not to limit the invention.

Example 1

Microfluidic Device

Figure 1:
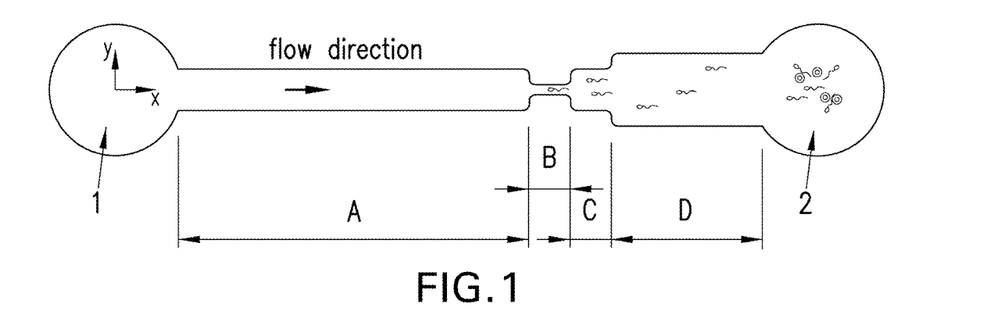
FIG. 1 is a diagram schematically showing one embodiment of the present invention.

Referring to FIG. 1, one embodiment of the microfluidic chip consists of a micro-channel with rectangular cross-sections, which is connected with fluid inlet 1 and sample inlet 2. The channel consists of 4 sections, namely sections A, B, C and D, with the same height of 25 µm and the widths of 1, 0.24, 1 and 1.74 mm, respectively. The channel width of sections B, C and D increases, while the ratio of their widths is set by reference to the sperm motility classification (SMC) criteria released by World Health Organization (WHO). The cross-sections of the channel in the present invention are rectangular, and the cross-sectional area is the product of the width and the height, so the cross-sectional areas increase. Because of Bernoulli's principle for incompressible flows, the velocity of the fluid decreases when the cross-sectional area of the channel increases.

In the present embodiment, the cross-sectional areas of section B, C and D increase successively, and each two sections (e.g., B and C, C and D) can be connected directly or by another connection channel. The cross-sectional area of the connection channel can be constant, or vary gradually, as long as its cross-sectional area should be larger than the smaller one of the two adjacent connected sections, more specifically, the size of connection channel between sections B and C should be larger than that of section B, while the size of connection channel between sections C and D should be larger than that of section C. In the present embodiment, the adjacent sections are connected directly. The section B with the largest cross-sectional area is connected to the sperm inlet 2, while section B with the smallest cross-sectional area is connected to the fluid inlet 1 with section A. In the present embodiment, section A serves as a fluid stabilizing zone, whose area is normally larger than section B. In other embodiments, if the fluid in sections A, B and C is stable enough, then section A can be omitted.

In the present embodiment, the channel can be covered by the oviduct epithelial cells of human or another animal, in order to more realistically mimic the physiological condition.

Figure 2:
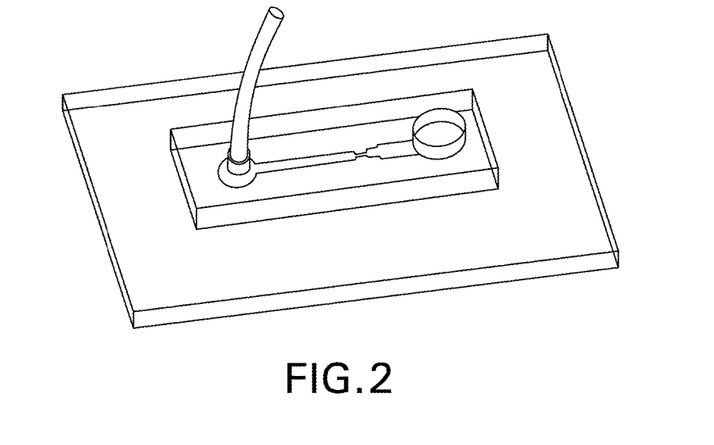
FIG. 2 is a three dimensional diagram schematically showing one embodiment of the present invention.

Referring to FIG. 2, the microfluidic device was constructed with one upper layer of PDMS and one lower layer of glass, following standard photolithography and micromolding procedures. The two layers were bonded irreversibly by oxygen plasma.

Figure 3:
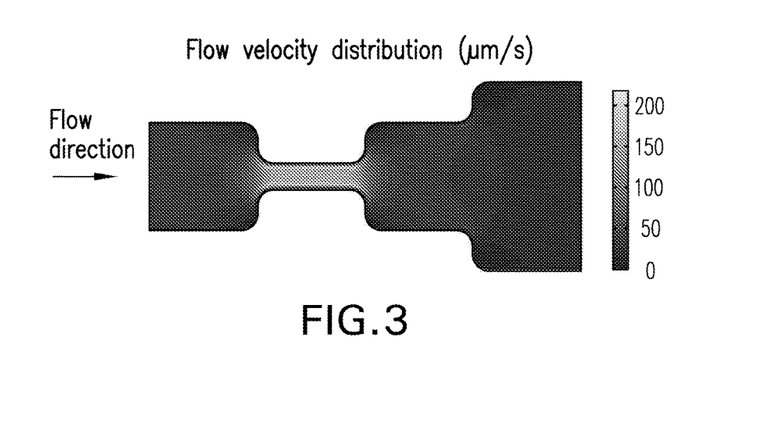
FIG. 3 is the fluidic field simulation results of one embodiment of the present invention, in which gray levels represent fluid velocity.
Figure 4:
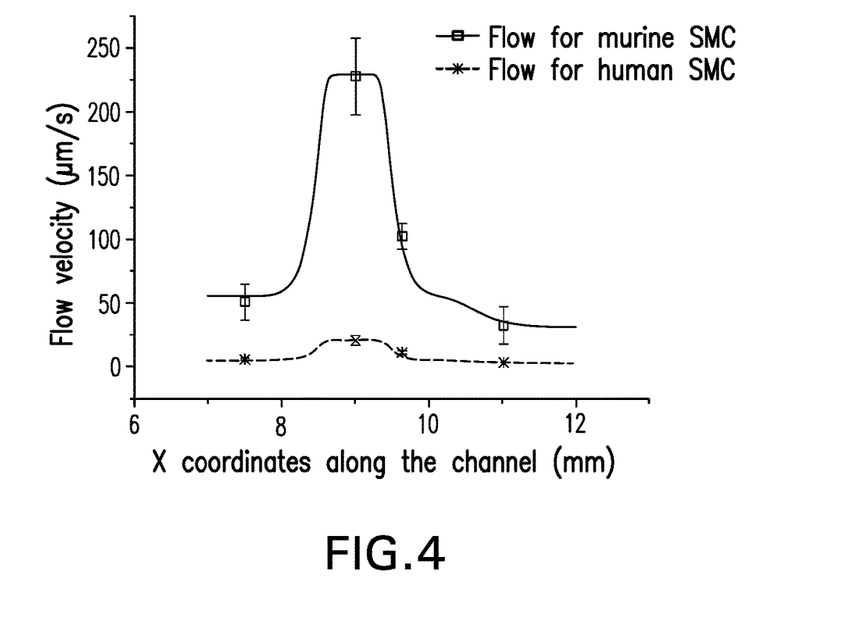
FIG. 4 is a line graph showing the real measurement results and simulation results of the fluidic field in one embodiment of the present invention.
Figure 5:
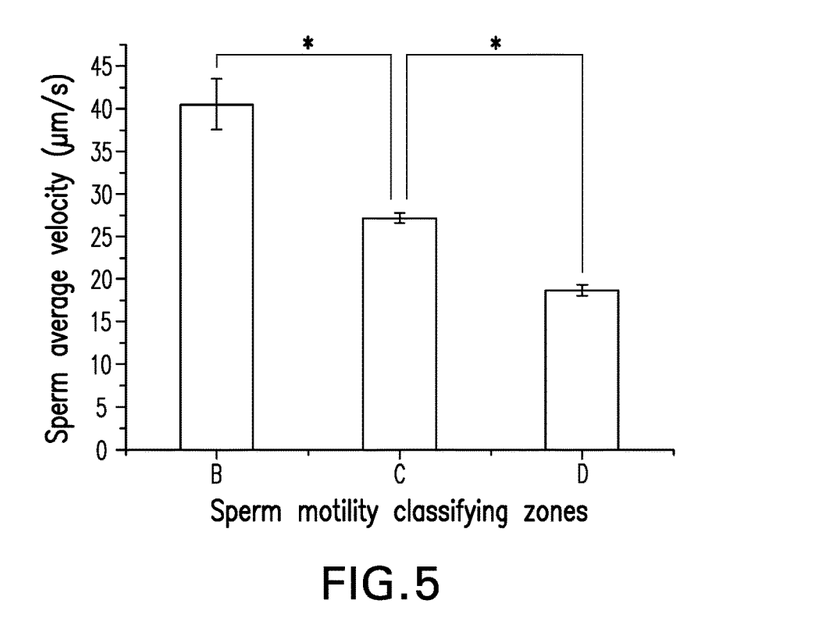
FIG. 5 is a bar graph showing the result of sperm motility classification.

Referring to FIG. 3, the flow in the channel was simulated by software. The model was based on the steady-state Navier-Stokes equation for an incompressible Newtonian fluid. The simulated results matched the design, i.e., the flow velocity decreases as the channel width increases. To examine the velocity distribution, culture medium mixed with microbeads (~3 µm in diameter, similar to sperm size) was loaded to fluid inlet 1 with different influx rates. Two separate influxes, i.e., 0.1 µL/min for murine SMC and 0.01 µl/min for human SMC, were tested respectively and results were shown in FIG. 4. FIG. 4 illustrates fluid velocity measurement results in the channel's center line using microbeads, whereas the squares and crosses represent the average measured velocity distribution in each section of the channel.

When the influx was 0.01 μL/min for human SMC, the velocity in sections A, B, C and D was 5.61±0.89, 20.29±4.06, 10.84±1.42, 3.00±0.56 μm/s, respectively, which was basically consistent with the current WHO criteria for human SMC. The result suggested that the device was able to form a predefined 4-grade velocity field with a wide range of applicable velocities (maximum velocity 20-220 μm/s), which is suitable for both human and murine sperm motility classification and capture.

Example 2

Integrated Mouse Sperm Motility Screening and Chemotaxis Assay

Sperm Motility Classification

The method to use the microfluidic chip as illustrated in FIG. 1 in the present embodiment is as follows: cell culture medium (or working solution) was influxed with certain flow rate from fluid inlet 1 by constant positive pressure from an injection pump, which resulted in a flow field with stable but different flow rates in sections A, B, C and D. The flow field was stabilized after 10 minutes, then 3 human semen sample (or 3 μL murine sperm solution) was pipetted into sperm inlet 2. Sperms swam against the flow and were trapped in the regions where a sperm's velocity equaled the local fluid flow velocity, resulting in that the combined velocity was zero. Thus, the motility of sperms trapped in sections B, C and D decreased in order, and the sperms with low motility as well as cells in semen that did not swim by themselves, e.g., spermatogonial cells, epithelial cells, white blood cells, etc., were left in sperm inlet 2.

Sperm Motility Evaluation in Different Sections

When the capture of sperms in sections B, C and D were completed, the injection pump was turned off and the positive pressure fluid was stopped, so as to let the sperm swim freely in static fluid. For sperm motility evaluation, 3 random fields of view were recorded for 10 seconds at a frame rate of 15 frames/s in each motility classifying section (B, C and D) respectively. The frames of the image series were then analyzed by software ImageJ 1.42q with Computer Assisted Sperm Analyzer (CASA) plugin, so that the amount of sperm in each zone as well as their motion parameters were calculated. The average VSL (40.5±3.0, 27.2±0.6 and 18.7±0.6 μm/s for B, C and D respectively) in different sections showed statistically significant differences.

Example 3

Retrieve or Research on the Sperm with Specific Velocity

When retrieving sperms with specific velocity, the culture medium influxed from fluid inlet is stopped. Sperms keep swimming spontaneously and arrive at the fluid inlet 1. Because sperms with different velocities are captured in section B, C and D, and the fastest sperms are the closest to the fluid inlet 1, sperms arrive at the fluid inlet 1 in order according to their velocities. This facilitates the recovery of sperms after motility classification.

The sperm can also be retrieved by the following methods: 1) apply a negative pressure at the fluid inlet 1, in order to transport sperm with different velocity captured in section B, C and D to the fluid inlet 1. The distances between the three sections and the fluid inlet 1 are different, so that sperms in various sections will arrive at different time; 2) a series of micro-electrodes are arranged along the bottom of the channel, and sperms with different velocities are captured in section B, C and D can be respectively retrieved at an outlet by dielectrophoresis.

If on-chip research, e.g., in vitro fertilization, is needed instead of the retrieval process, sperms with specific velocity can be transported to target zones on the chip instead of the fluid inlet 1.

Example 4

Another Microfluidic Chip

Figure 6:
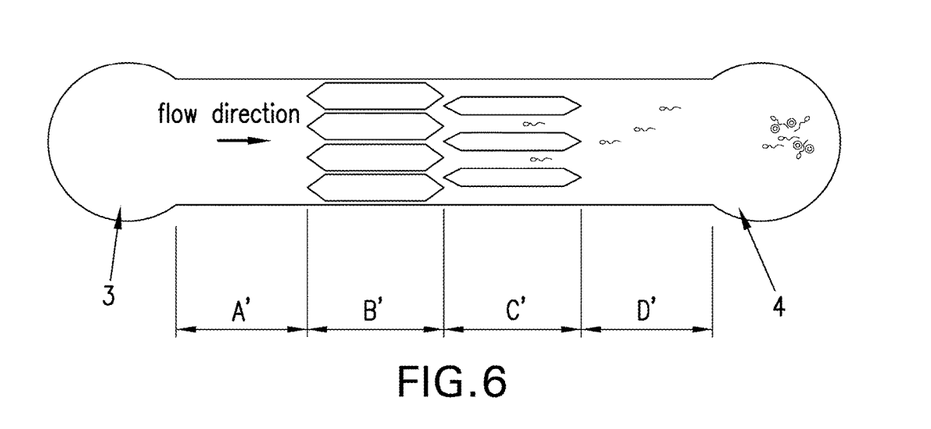
FIG. 6 is a diagram schematically showing another embodiment of the present invention.
Figure 7:
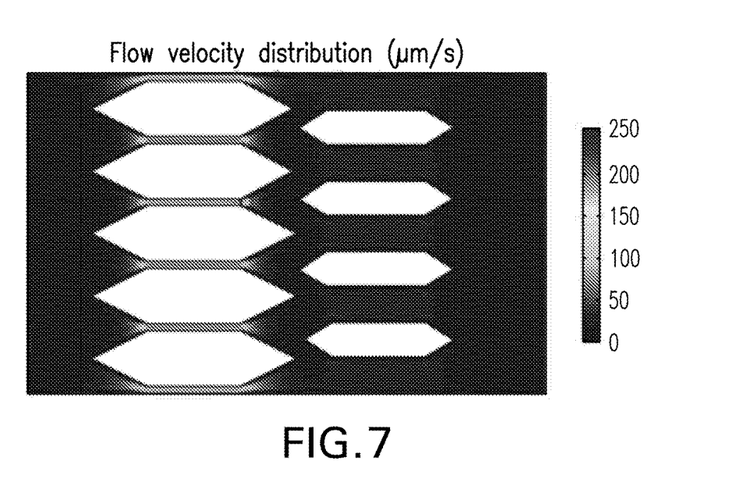
FIG. 7 is the fluidic field simulation results of another embodiment of the present invention, in which gray levels represent fluid velocity.

FIG. 6 illustrates another embodiment of the microfluidic chip in the present invention. The cross section is rectangular, and the velocity in different sections is achieved by changing the shape of the cross sections, e.g., by adding a series of fluid barriers with various widths. Either changing the number or the width of the fluid barriers inside the channel is applicable. The fluid barriers can be any shape, with the preferred shape being that both ends in the direction of fluid flow are acute angles, so that sperms will not be blocked by the barriers. The shape of the fluid barriers in the present embodiment is hexagonal. FIG. 7 is the fluidic field simulation results of the present embodiment.

Referring to FIG. 6, inlet 3 is the fluid inlet, and inlet 4 is the sperm inlet; the inlets 3 and 4 are connected by 4 sections A', B', C' and D' in order, in which the widths of barriers in section B', C' and D' gradually decrease, while their numbers also decrease (no barrier in section D'). Thus the cross-sectional areas gradually increase, while fluid velocity decreases. Section A' serves as the fluid stabilizing zone. The cross-sectional area of A' is normally larger than that of B'. In the present embodiment, there is no barrier in section A' or D', so that their cross-sectional areas are the same.

The above examples are included for illustrative purposes only and are not intended to limit the scope of the invention. Many variations to those described above are possible. Since modifications and variations to the examples described above will be apparent to those of skill in this art, it is intended that this invention be limited only by the scope of the appended claims.

We claim:

1. A microfluidic device for classification of the motility of a cell, which microfluidic device comprises:
    a fluid inlet,
    a sample inlet, and
    a channel connecting said fluid inlet and said sample inlet,
        wherein said channel comprises at least three sections of different cross-sectional areas, and said channel allows fluid flow from said fluid inlet to said sample inlet, wherein the ratio of the cross-sectional areas of the three different channel sections is about 0.24::1::1.74,
    wherein the cross-sectional area of each section increases successively in the direction from the fluid inlet to the sample inlet, and the section having the largest cross-sectional area is connected to the sample inlet, and
    wherein the section having the smallest cross-sectional area is connected directly to die fluid inlet, or wherein the section having the smallest cross-sectional area is connected to the fluid inlet through a first fluid stabilizing zone and the section having the smallest cross-sectional area is connected directly to the first fluid stabilizing zone.

2. The microfluidic device of claim 1, wherein the channel sections with different cross-sectional areas comprise barriers of different sizes, numbers and/or arrangements.

3. The microfluidic device of claim 1, wherein the adjacent sections of different cross-sectional areas are connected directly to each other or through a second fluid stabilizing zone.

4. The microfluidic device of claim 2, wherein the barriers comprise epithelial cells.

5. The microfluidic device of claim 1, wherein the channel is covered by epithelial cells.

6. The microfluidic device of claim 1, further comprising a cell culture medium, wherein the cell culture medium flows in the channel from the fluid inlet to the sample inlet.

7. The microfluidic device of claim 6, wherein the maximum flow rate of the cell culture medium is about 20-220 µm/s.

8. The microfluidic device of claim 7, wherein the maximum flow rate of the cell culture medium is about 20 µm/s.

9. The microfluidic device of claim 6, further comprising a cell in the cell culture medium.

10. The microfluidic device of claim 9, wherein the cell is a sperm.

11. The microfluidic device of claim 1, wherein a chemo-attractant is applied in the fluid inlet.

12. The microfluidic device of claim 11, wherein the chemo-attractant is progesterone, a growth factor, or glucose.

13. The microfluidic device of claim 1, wherein the channel comprises at least two electrodes.

14. A system for classifying cell motility, which comprises the microfluidic device of claim 1 and an apparatus to apply force to the cell culture medium.

15. The system of claim 14, further comprising a measuring device to measure the motility of the cell.

16. The system of claim 15, wherein the measuring device is a camera or video recorder.

17. A method of classifying the motility of a cell using the microfluidic device of claim 1 comprising:
    a) adding a cell culture medium in the fluid inlet;
    b) adding a cell in the sample inlet;
    c) applying an external force to the cell culture medium to achieve a flow rate; and
    d) measuring the motility of the cell moving against the flow of the culture medium in the channel.

18. The method of claim 17, wherein cells with different motilities locate in different sections of the channel.

19. The method of claim 17, wherein a chemo-attractant is applied in the fluid inlet, wherein the chemo-attractant is progesterone, a growth factor, or glucose.

20. The method of claim 17, wherein the motility of the cell is measured by taking a picture or video of the cell in the channel or by the location of the cell in different sections of the channel.

21. The method of claim 17, wherein the flow of the cell culture medium is stopped to let the cell move to the fluid inlet.

22. The method of claim 21, wherein an external force is applied to the cell, wherein the external force is an electrical force, an optical force or a fluidic force.

23. The method of claim 21, wherein the cell with a specific motility is retrieved.

24. The method of claim 17, wherein a plurality of cells are added in the sample inlet and the cells are sperms.

25. The method of claim 24, wherein one or more of the sperms are used for in vitro fertilization.

26. The microfluidic device of claim 4, wherein the epithelial cells are oviduct epithelial cells.

27. The microfluidic device of claim 5, wherein the epithelial cells are oviduct epithelial cells.

28. The microfluidic device of claim 1, wherein the cross-sectional area of the first fluid stabilizing zone is larger than the cross-sectional area of the section of the channel having the smallest cross-sectional area.

29. The microfluidic device of claim 3, wherein the cross-sectional area of the second fluid stabilizing zone is constant or variant.

30. The microfluidic device of claim 3, wherein the cross-sectional area of the second fluid stabilizing zone is larger than the cross-sectional area of any adjacent section of the channel.

* * * * *